(12) United States Patent
Chew et al.

(10) Patent No.: US 7,432,377 B2
(45) Date of Patent: Oct. 7, 2008

(54) QUINOLINE INTERMEDIATES OF RECEPTOR TYROSINE KINASE INHIBITORS AND THE SYNTHESIS THEREOF

(75) Inventors: Warren Chew, Outremont (CA); Maria Papamichelakis, Montreal (CA); Youchu Wang, St. Laurent (CA)

(73) Assignee: Wyeth, Madison, NJ (US)

( * ) Notice: Subject to any disclaimer, the term of this patent is extended or adjusted under 35 U.S.C. 154(b) by 533 days.

(21) Appl. No.: 11/036,408

(22) Filed: Jan. 14, 2005

(65) Prior Publication Data

US 2005/0159446 A1 Jul. 21, 2005

Related U.S. Application Data

(60) Provisional application No. 60/537,329, filed on Jan. 16, 2004.

(51) Int. Cl.
C07D 215/38 (2006.01)
(52) U.S. Cl. .................... 546/159; 546/160
(58) Field of Classification Search ........... 546/159, 546/160
See application file for complete search history.

(56) References Cited

U.S. PATENT DOCUMENTS

| 6,297,258 B1 | 10/2001 | Wissner et al. | 514/313 |
|---|---|---|---|
| 6,617,333 B2 | 9/2003 | Rabindran et al. | 514/291 |
| 7,009,053 B2 * | 3/2006 | Kim et al. | 546/159 |
| 7,126,025 B2 | 10/2006 | Considine et al. | 562/868 |

FOREIGN PATENT DOCUMENTS

| WO | WO 98/43960 | 10/1998 |
|---|---|---|
| WO | WO 98/54158 | 12/1998 |
| WO | WO 00/18740 | 6/2000 |
| WO | WO 00/031049 | 6/2000 |
| WO | WO 00/68201 | 11/2000 |
| WO | WO 01/55116 A2 | 8/2001 |
| WO | WO 02/36570 | 5/2002 |
| WO | WO 2005/070890 | 8/2005 |
| WO | WO 2006/117570 | 11/2006 |

OTHER PUBLICATIONS

Tominaga et al., J. Heterocyclic Chem., 27, pp. 1217-1225 (1990).
Price and Boekelheide, "A Synthesis of Substituted 4-Aminoquinolines," J. Am. Chem. Soc., vol. 68, pp. 1246-1250, 1946.
Meth-Cohn et al., "The Reverse Vilmeier Approach to the Synthesis of Quinolines, Quinolinium Salts and Quinolones", Tetrahedron, vol. 51 (47), pp. 12869-12882, 1995.
R. M. Roberts and P. J. Vogt, J. Am. Chem. Soc., 78, 4778 (1956).
R. J. Jones, J. Am. Chem. Soc., 74, 4889 (1952).
U. Jordis, F. Sauter and M. Burkart, J. Prakt. Chem., 333 (2), 267 (1991).
H. Agui, T. Komatsu and T. Nakagome, J. Heterocyclic Chem., 12, 557 (1975).
H. Agui, T. Mitani, M. Nakashita and T. Nakagome, J. Heterocyclic Chem., 8, 357 (1971).
R.M. Roberts, J. Am. Chem. Soc., 71, 3848 (1949).
R.M. Roberts and R.H. DeWolfe, J. Am. Chem. Soc., 76, 2411 (1954).

* cited by examiner

*Primary Examiner*—D. Margaret Seaman
(74) *Attorney, Agent, or Firm*—Fitzpatrick, Cella, Harper & Scinto

(57) ABSTRACT

This invention is directed to methods of preparing 4-substituted quinoline compounds as intermediates in the manufacture of receptor tyrosine kinase inhibitors and intermediate compounds used in the methods thereof, wherein the 4-substituted quinoline compound has the following general formula (I):

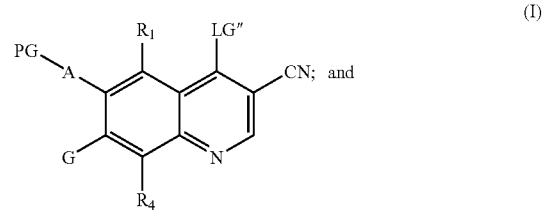

(I)

wherein substitutions at LG'', PG, A, G, $R_1$ and $R_4$ are set forth in the specification.

2 Claims, No Drawings

QUINOLINE INTERMEDIATES OF RECEPTOR TYROSINE KINASE INHIBITORS AND THE SYNTHESIS THEREOF

This application claims the benefit of U.S. Provisional Application No. 60/537,329, filed on Jan. 16, 2004.

BACKGROUND OF THE INVENTION

1. Field of the Invention

This invention is directed to methods of preparing 4-substituted quinoline compounds as intermediates in the manufacture of receptor tyrosine kinase inhibitors and intermediate compounds used in the methods thereof.

2. Related Background Art

Protein tyrosine kinases (PTKs) are critical in regulating cell growth and differentiation. One general class of PTK is the receptor tyrosine kinase (RTK). Once activated, usually through the binding of a ligand, an RTK initiates signaling for various activities, such as cell growth and replication.

The RTKs comprise one of the larger families of PTKs and have diverse biological activity. At present, at least nineteen (19) distinct subfamilies of RTKs have been identified. One such subfamily is the "HER" family of RTKs, which includes epidermal growth factor receptor (EGFR), ErbB2 (HER2), ErbB3 (HER3) and ErbB4 (HER4).

Under certain conditions, as a result of either mutation or over expression, studies have shown that these RTKs can become deregulated; the result of which is uncontrolled cell proliferation which can lead to tumor growth and cancer (Wilks, A. F., Adv. Cancer Res., 60, 43 (1993) and Parsons, J. T.; Parsons, S. J., Important Advances in Oncology, DeVita, V. T. Ed., J. B. Lippincott Co., Phila., 3 (1993)). For example, over expression of the receptor kinase product of the ErbB2 oncogene has been associated with human breast and ovarian cancers (Slamon, D. J. et al., Science, 244, 707 (1989) and Science, 235, 177 (1987)).

In addition, deregulation of EGFR kinase has been associated with epidermoid tumors (Reiss, M., et al., Cancer Res., 51, 6254 (1991)), breast tumors (Macias, A. et al., Anticancer Res., 7, 459 (1987)), and tumors involving other major organs (Gullick, W. J., Brit. Med. Bull., 47, 87 (1991)).

These RTKs are known to also be involved in processes crucial to tumor progression, such as apoptosis, angiogenesis and metastasis.

Therefore, inhibitors of these RTKs have potential therapeutic value for the treatment of cancer and other diseases characterized by uncontrolled or abnormal cell growth. Accordingly, many recent studies have dealt with the development of specific RTK inhibitors as potential anti-cancer therapeutic agents (e.g., Traxler, P., Exp. Opin. Ther. Patents, 8, 1599 (1998) and Bridges, A. J., Emerging Drugs, 3, 279 (1998)).

Quinoline derivatives are known to be important intermediate compounds in the synthesis of RTK inhibitors. For example, in the following US patents, quinoline derivatives are disclosed and the compounds are stated to be involved in inhibiting PTK activity: U.S. Pat. No. 6,288,082 (Sep. 11, 2001) and U.S. Pat. No. 6,297,258 (Oct. 2, 2001).

In addition, various methods for the preparation of quinoline derivatives are known in the art, but these methods contain serious limitations. One such method is the thermal cyclization reaction. (Sabnis, R. W., et al., J. Hetero. Chem., 29, 65 (1992); Mehta, N. C., et al., J. Ind. Chem. Soc., 55(2), 193 (1978); Bredereck, H., et al., Chem. Ber., 98(4), 1081 (1965); Salon, J., et al., fur Chem., 131, 293 (2000)). Although commonly used, this method requires high temperature conditions, which limits its use for large-scale production of quinoline and quinoline derivatives. This method also requires high dilution conditions, which results in an overall decrease in throughput. Furthermore, the yields from thermal cyclization reactions are typically 50% or less.

Another limitation is that many reactions used in preparing quinoline derivatives often generate unwanted by-products. For example, the chlorination reaction used in preparing quinoline derivatives suffers from the generation of viscous tars and decomposition products that are difficult to clean and remove, which results in yields that vary widely, typically in the range from 24-64%.

Recently, there has been research into other methods for the preparation of quinoline derivatives. One such method involves the use of microwave-assisted methodology for the preparation of quinolones from aromatic amines. (Dave, C. G., et al., Ind. J. Chem., 41B, 650 (2002)). However, these newer methods also suffer from the same foregoing limitations, such as the high temperature conditions requirement.

Accordingly, there continues to be a need for novel quinoline compounds used in the preparation of RTK inhibitors and methods of preparing such quinoline compounds without the foregoing limitations. In particular, there is a need for methods of preparing such quinoline compounds without the requirement of high temperature conditions.

SUMMARY OF THE INVENTION

This invention relates to methods of preparing 4-substituted quinoline compounds as intermediates in the manufacture of RTK inhibitors and intermediates used in the methods thereof.

Thus, in one aspect, the present invention is a method of preparing a 4-substituted quinoline compound comprising the step of reacting a compound of formula (II):

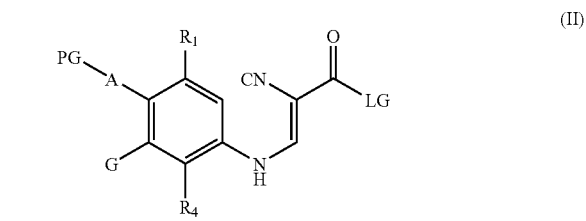

with a reagent of formula POLG'$_3$, wherein LG' is halo, to provide a compound of formula (I):

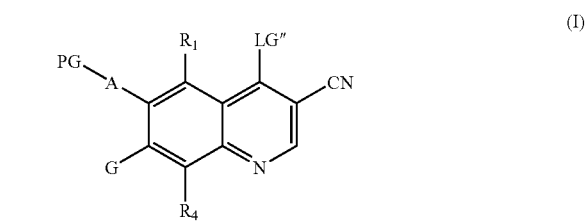

wherein LG is a leaving group selected from the group consisting of morpholine, o-mesyl, o-tosyl, triflate, LG" is a leaving group selected from the group consisting of morpholine, o-mesyl, o-tosyl, triflate, or halogen; PG is a protecting group selected from the group consisting of acyl, $CH_3OC(O)-$, $EtOC(O)-$, Fmoc, trifluoroacetamide, Troc, Phenoc, benzamide, Teoc and cyclic imides such as pthalimide, maleimide and 2,5-dimethylpyrrole; A is O, NR, or S, R is H, alkyl, alkenyl or alkynyl; and G, $R_1$ and $R_4$ are each, independently, hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phthalimide, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

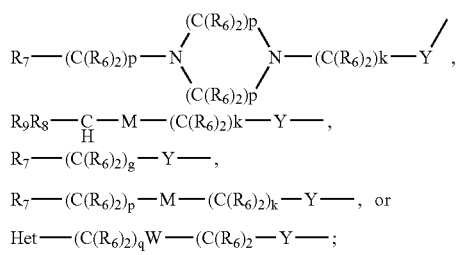

or $R_1$ and $R_4$ are as defined above and G is $R_2$—NH—;

or if any of the substituents $R_1$, $R_4$ or G are located on contiguous carbon atoms then they may be taken together as the divalent radical —O—$C(R_6)_2$—O;

Y is a divalent radical selected from the group consisting of

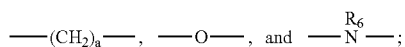

$R_7$ is —$NR_6$, —$OR_6$, -J, —$N(R_6)_3^+$, or —$NR_6(OR_6)$;

M is >$NR_6$, —O—, >N—$(C(R_6)_2)_p NR_6 R_6$, or >N—$(C(R_6)_2)_p$—$OR_6$;

W is >NR6, —O—or is a bond;

Het is is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

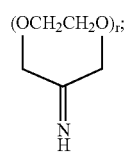

wherein Het is optionally mono- or di-substituted on carbon or nitrogen with $R_6$, optionally mono- or di-substituted on carbon with hydroxy, —$N(R_6)_2$, or —$OR_6$, optionally mono or di-substituted on carbon with the mono-valent radicals —$(C(R_6)_2)_s OR_6$ or —$(C(R_6)_2)_s N(R_6)_2$, and optionally mono or di-substituted on a saturated carbon with divalent radicals —O— or —$O(C(R_6)_2)_s O$—;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms; with the proviso that the alkenyl or alkynyl moiety is bound to a nitrogen or oxygen atom through a saturated carbon atom;

$R_2$, is selected from the group consisting of

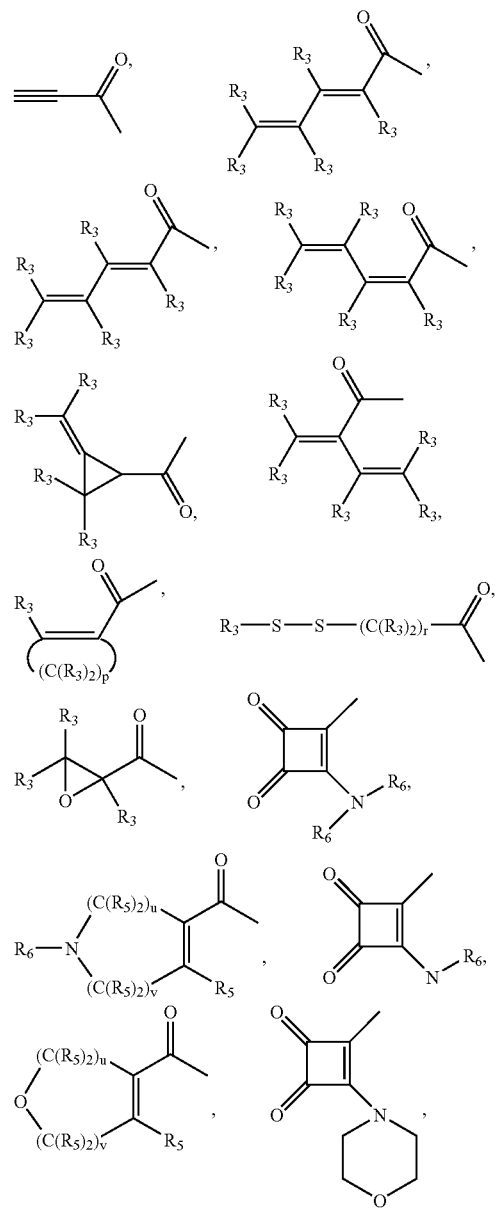

-continued

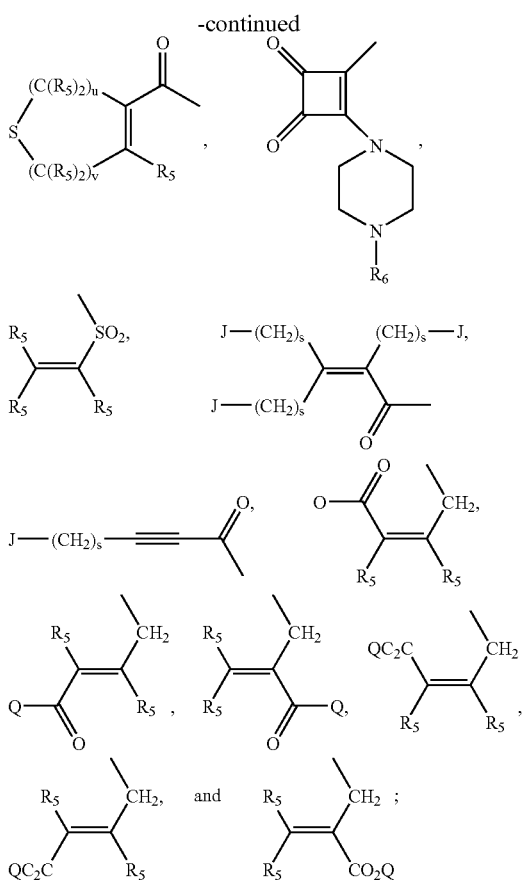

$R_3$ is independently hydrogen, alkyl of 1-6 carbon atoms, carboxy, carboalkoxy of 1-6 carbon atoms, phenyl, carboalkyl of 2-7 carbon atoms,

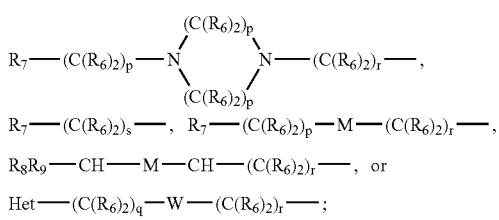

$R_5$ is independently hydrogen, alkyl of 1-6 carbon atoms, carboxy, carboalkoxy of 1-6 carbon atoms, phenyl carboalkyl of 2-7 carbon atoms,

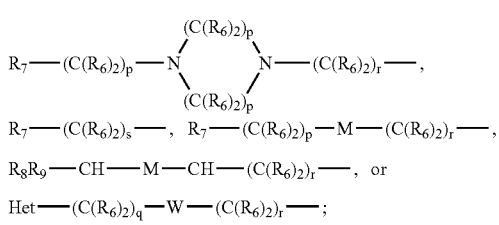

$R_8$, and $R_9$ are each independently $-(C(R_6)_2)_rNR_6R_6$, or $-(C(R_6)_2)_rOR_6$;

J is independently hydrogen, chlorine, fluorine, or bromine;

Q is an alkyl of 1-6 carbon atoms or hydrogen;

a=0 or 1;
g=1-6;
k=0-4;
n is 0-1;
m is 0-3;
p=2-4;
q=0-4;
r=1-4;
s=1-6;
u=0-4 and v=0-4, wherein the sum of u+v is 2-4;
x=0-3;
y=0-1;
z=0-3;

or a salt thereof.

The present invention is also directed to a method of synthesizing a compound of formula (VIII):

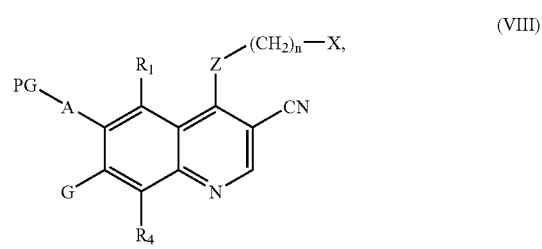

comprising the steps of:

a. reacting a compound of formula (I):

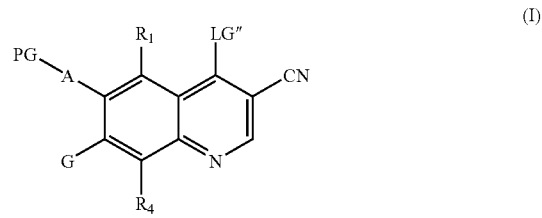

with a nucleophilic reagent of formula HZ-(CH$_2$)$_n$—X; or b(i). reacting a compound of formula (II):

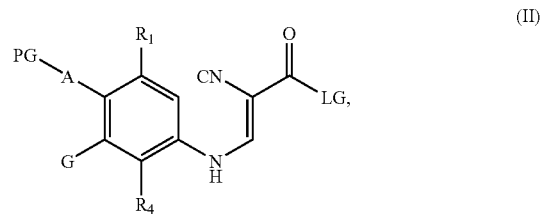

with a nucleophilic reagent of formula HZ-(CH$_2$)$_n$—X to form a compound of formula (IX):

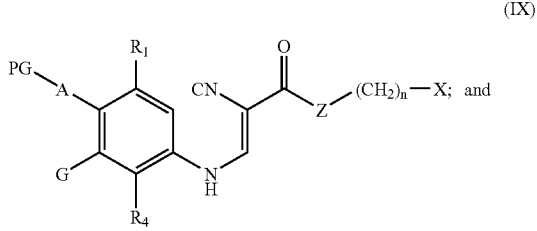

b(ii). cyclizing the compound of formula (IX) with a reagent of formula POLG' to produce the compound of formula (VIII).

wherein LG, LG', LG'', PG, A, G, $R_1$ and $R_4$ are as defined above, and Z can be NR, O or S, n is 0 or 1, and X can be cycloalkyl of 3 to 7 carbon atoms, which may be optionally substituted with one or more alkyl of 1 to 6 carbon atom groups, or is a pyridinyl, pyrimidinyl, or phenyl ring, wherein the pyridinyl, pyrimidinyl, or phenyl ring may be optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or X can be a bicyclic aryl or bicyclic heteroaryl ring system of 8 to 12 atoms, where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkyl amino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or X can be a radical having the formula:

$$\diagup^{A'}\diagdown_T\diagup^L,$$

wherein A' is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamnino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, T is bonded to a carbon of A' and is:

—NH($CH_2$)$_m$—, —O($CH_2$)$_m$—, —S($CH_2$)$_m$—, —NR($CH_2$)$_m$—,
—($CH_2$)$_m$— —($CH_2$)$_m$NH—, —($CH_2$)$_m$O—, —($CH_2$)$_m$S—, or —($CH_2$)$_m$NR—;

and L is an unsubsitituted phenyl ring or a phenyl ring mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or L can be a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkylof 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino.

In another aspect, the present invention is an intermediate aryl-2-propenamide compound used in the foregoing method of preparing a 4-substituted quinoline compound of formula (I), the aryl-2-propenamide compound having the following formula (II):

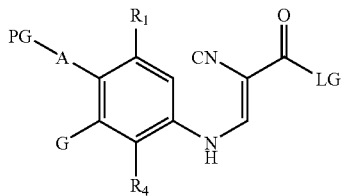

wherein LG, PG, A, G, $R_1$ and $R_4$ are as defined above.

DETAILED DESCRIPTION OF THE INVENTION

The compounds of formulas (I), (II) and (VIII) can be readily prepared according to the following reaction schemes or modification thereof. In the following reaction schemes LG, LG', LG", X, PG, A, G, $R_1$ and $R_4$ are selected from the groups defined above.

Scheme 1 illustrates preferred embodiments of the method of preparing a 4-substituted quinoline compound.

Troc, Phenoc, benzamide, Teoc and cyclic imides such as pthalimide, maleimide and 2,5-dimethylpyrrole at the substituted A attached to the 6-position of the quinoline ring system.

The method of preparing quinoline compounds of the present invention has multiple distinct advantages over previous methods of preparing quinoline core compounds. Most significantly, a high temperature (e.g., 250° C.) cyclization step is not required for the present method. In addition, the present method generates little or no insoluble and viscous tars; and the formation of decomposition products is minimized. Furthermore, the current method reduces the number of steps required to prepare the desired quinoline compounds.

The method depicted in Scheme 1 shows that compound of formula (II) can be converted to a compound of formula (I) via formation of intermediate (VII). However, the intermediate of formula (VII) can also be isolated. Therefore, this method allows a quinoline compound to be formed with a variety of leaving groups at the 4-position. These quinoline compounds can then be further substituted by reacting them with a nucleophilic reagent.

With these advantages, the present method overcomes many of the limitations of previous methods, resulting in

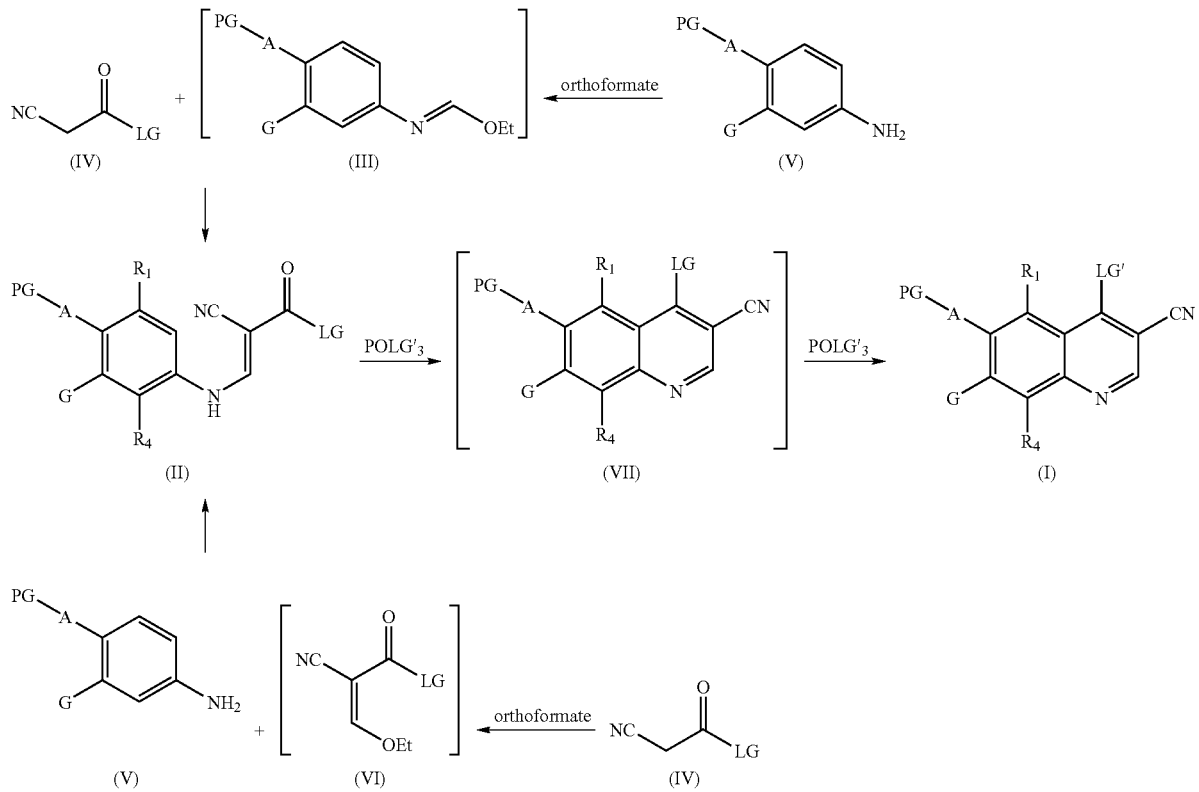

In Scheme 1, LG, LG', LG", PG, A, G, $R_1$ and $R_4$ are as defined above.

The quinoline compounds of the present invention have a protecting group (PG) selected from the group consisting of acyl, $CH_3OC(O)-$, $EtOC(O)-$, Fmoc, trifluoroacetamide, higher throughput and a more cost-effective way to prepare quinoline core compounds for use in the manufacture of RTK inhibitors.

In a preferred embodiment, the compounds of formula (I), (II) and (VIII) are subject to the following provisos:

When $R_6$ is an alkenyl of 2-7 carbon atoms or alkynyl of 2-7 carbon atoms, such alkenyl or alkynyl moiety is bound to a nitrogen or oxygen atom through a saturated carbon atom.

Further, when Y is —$NR_6$— and $R_7$ is —$NR_6R_6$, —N($R_6$)$_3^+$, or —$NR_6(OR_6)$, then g=2-6; when M is —O— and $R_7$ is —$OR_6$ then p=1-4; when Y is —$NR_6$— then k=2-4; when Y is —O— and M or W is —O— then k=1-4; when W is not a bond with Het bonded through a nitrogen atom then q=2-4; and when W is a bond with Het bonded through a nitrogen atom and Y is —O— or —$NR_6$— then k=2-4.

For purposes of this invention the term "alkyl" includes both straight and branched alkyl moieties, which can contain as many as 12 carbon atoms. Preferably, the alkyl moiety contains between 1 to 6 carbon atoms, though 1 to 4 carbon atoms is more preferable. The term "alkenyl" refers to a radical aliphatic hydrocarbon containing one double bond and includes both straight and branched alkenyl moieties of 2 to 6 carbon atoms. Such alkenyl moieties may exist in the E or Z configurations; the compounds of this invention include both configurations. The term "alkynyl" includes both straight chain and branched moieties containing 2 to 6 carbon atoms having at least one triple bond. The term "cycloalkyl" refers to alicyclic hydrocarbon groups having 3 to 12 carbon atoms and includes but is not limited to: cyclopropyl, cyclobutyl, cyclopentyl, cyclohexyl, cycloheptyl, norbornyl, or adamantyl.

For purposes of this invention the term "aryl" is defined as an aromatic hydrocarbon moiety and may be substituted or unsubstituted. An aryl group preferably contains 6 to 12 carbon atoms and may be selected from, but not limited to, the group: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups. An aryl group may be optionally mono-, di-, tri- or tetra-substituted with substituents selected from, but not limited to, the group consisting of alkyl, acyl, alkoxycarbonyl, alkoxy, alkoxyalkyl, alkoxyalkoxy, cyano, halogen, hydroxy, nitro, trifluoromethyl, trifluoromethoxy, trifluoropropyl, amino, alkylamino, dialkylamino, dialkylaminoalkyl, hydroxyalkyl, alkoxyalkyl, alkylthio, —$SO_3H$, —$SO_2NH_2$, —$SO_2NHalkyl$, —$SO_2N(alkyl)_2$, —$CO_2H$, $CO_2NH_2$, —$CO_2NHalkyl$, and —$CO_2N(alkyl)_2$. Preferred substituents for aryl and heteroaryl include: alkyl, halogen, amino, alkylamino, dialkylamino, trifluoromethyl, trifluoromethoxy, arylalkyl, and alkylaryl.

For purposes of this invention the term "heteroaryl" is defined as an aromatic heterocyclic ring system (monocyclic or bicyclic) where the heteroaryl moieties are five or six membered rings containing 1 to 4 heteroatoms selected from the group consisting of S, N, and O, and include but is not limited to: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1 H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, pyrrolidinyl; (2) a bicyclic aromatic heterocycle where a phenyl, pyridine, pyrimidine or pyridizine ring is: (i) fused to a 6-membered aromatic (unsaturated) heterocyclic ring having one nitrogen atom; (ii) fused to a 5 or 6-membered aromatic (unsaturated) heterocyclic ring having two nitrogen atoms; (iii) fused to a 5-membered aromatic (unsaturated) heterocyclic ring having one nitrogen atom together with either one oxygen or one sulfur atom; or (iv) fused to a 5-membered aromatic (unsaturated) heterocyclic ring having one heteroatom selected from O, N or S. Preferably a bicyclic heteroaryl group contains 8 to 12 carbon atoms.

For the purposes of this invention the term "alkoxy" is defined as $C_1$-$C_6$-alkyl-O—; wherein alkyl is as defined above.

For purposes of this invention the term "alkanoyloxymethyl" is defined as —$CH_2OC(O)R$, wherein R is alkyl of 1 to 6 carbon atoms.

The terms "alkylaminoalkoxy" and "dialkylaminoalkoxy" refer to alkylamino and dialkylamino moieties with one or two alkyl groups (the same or different) bonded to the nitrogen atom which is attached to an alkoxy group of 1 to 6 carbon atoms. Preferably a dialkylaminoalkoxy moiety consist of 3 to 10 carbon atoms and a alkylaminoalkoxy moiety consist of from 2 to 9 carbon atoms.

For purposes of this invention the term "alkylthio" is defined as $C_1$-$C_6$-alkyl-S.

For purposes of this invention "alkoxyalkyl" and "alkylthioalkyl" denote an alkyl group as defined above that is further substituted with an alkoxy or alkylthio as defined above. A preferred alkoxyalkyl moiety is alkoxymethyl (e.g. alkoxy-$CH_2$—).

For purposes of this invention the term "hydroxy" is defined as a HO-moiety. Furthermore, for purposes of this invention the term "hydroxylalkyl" is defined as a HO-alkyl-moiety, wherein the alkyl moiety consist of 1 to 6 carbons.

For purposes of this invention the term "benzoylamino" is defined as a Ph-OC(O)NH-moiety.

The terms "monoalkylamino" and "dialkylamino" refer to moieties with one or two alkyl groups wherein the alkyl chain is 1 to 6 carbons and the groups may be the same or different. The terms "monoalkylaminoalkyl" and "dialkylaminoalkyl" refer to monoalkylamino and dialkylamino moieties with one or two alkyl groups (the same or different) bonded to the nitrogen atom which is attached to an alkyl group of 1 to 6 carbon atoms. Preferably a dialkylaminoalkyl moiety consist of 3 to 10 carbon atoms and a alkylaminoalkyl moiety consist of from 2 to 9 carbon atoms.

For purposes of this invention the term "mercapto" is defined as a —SH moiety.

For purposes of this invention the term "carboxy" is defined as a —COOH moiety.

For purposes of this invention the term "alkenoylamino" and "alkynoylamino" are defined as a —NH—COOR moiety, wherein R is alkenyl or alkynyl of 3 to 8 carbon atoms.

For purposes of this invention the term "carboalkoxy" is defined as —$CO_2R$, wherein R is alkyl of 1 to 6 carbon atoms.

For purposes of this invention the term "carboalkyl" is defined as —COR, wherein R is alkyl of 1 to 6 carbon atoms.

For purposes of this invention the term "carboxyalkyl" is defined as a HOOCR-moiety, wherein R is alkyl of 1 to 6 carbon atoms.

For purposes of this invention the term "carboalkoxyalkyl" is defined as a —R—$CO_2$—R' moiety, wherein R and R' are alkyl and together consist of from 2 to 7 carbon atoms.

For purposes of this invention the term "aminoalkyl" is defined as $H_2N$-alkyl, wherein the alkyl group consist of 1 to 5 carbon atoms.

"Azido" is a radical of the formula —$N_3$.

For purposes of this invention the term "alkanoylamino" is defined as a —NH—COOR moiety, wherein R is alkyl of 1 to 6 carbon atoms.

"Acyl" is a radical of the formula —(C=O)-alkyl or —(C=O)-perfluoroalkyl wherein the alkyl radical or perfluoroalkyl radical is 1 to 6 carbon atoms; preferred examples include but are not limited to, acetyl, propionyl, butyryl, trifluoroacetyl.

For purposes of this invention the term "alkylsulfinyl" is defined as a R'SO-radical, where R' is an alkyl radical of 1 to 6 carbon atoms. Alkylsulfonyl is a R'$SO_2$-radical, where R' is an alkyl radical of 1 to 6 carbon atoms. Alkylsulfonamido, alkenylsulfonamido, alkynylsulfonamido are R—$SO_2NH$-radicals, where R' is an alkyl radical of 1 to 6 carbon atoms, an alkenyl radical of 2 to 6 carbon atoms, or an alkynyl radical of 2 to 6 carbon atoms, respectively.

The term "substituent" is used herein to refer to an atom radical, a functional group radical or a moiety radical that replaces a hydrogen radical on a molecule. Unless expressly stated otherwise, it should be assumed that any of the substituents may be optionally substituted with one or more groups selected from: alkyl, halogen, haloalkyl, hydroxyalkyl, nitro, amino, hydroxy, cyano, alkylamino, dialkylamino, alkoxy, haloalkoxy, alkoxyalkyl, alkoxyalkoxy, oxo, alkylthio, mercapto, haloalkylthio, aryl, aryloxy, arylthio, heteroaryl, heteroaryloxy, heteroarylthio, acyl, —$CO_2$-alkyl, —$SO_3H$, —$SO_2NH_2$, —$SO_2NH$-alkyl, —$SO_2NH$—(alkyl)$_2$, —$CO_2H$, —$CO_2NH_2$, —$CO_2NH$-alkyl and —$CO_2N$—(alkyl)$_2$.

For purposes of this invention, a "halogen" is one of the non-metallic elements found in group VII A of the periodic table. Accordingly, a halogen of the present invention is a monovalent moiety which is derived from fluorine, chlorine, bromine, iodine or astatine. Preferred halogens are selected from the group consisting of chloro, fluoro and bromo.

For the purposes of this invention the term "substituted" refers to where a hydrogen radical on a molecule has been replaced by another atom radical, a functional group radical or a moiety radical; these radicals being generally referred to as "substituents."

For purposes of this invention, the term "protecting group" refers to a group introduced into a molecule to protect a sensitive functional group or specific position on the molecule from reacting when the molecule is exposed to reagents or conditions to transform or react another part of the molecule. Thereafter the protecting group can be removed. Suitable protecting groups are well known in the art and include acid-labile, base-labile, photoremovable, or removable under neutral conditions. See, e.g., Green, Protecting Groups in Organic Synthesis, Wiley, pp. 218-288 (1985), which is incorporated herein by reference.

For the present invention, suitable protecting groups are of acyl, $CH_3OC(O)$—, $EtOC(O)$—, Fmoc, trifluoroacetamide, Troc, Phenoc, benzamide, Teoc and cyclic imides such as pthalimide, maleimide and 2,5-dimethylpyrrole. In one preferred embodiment, the protecting group is acyl.

The compounds of this invention may contain an asymmetric carbon atom and may thus give rise to stereoisomers, such as enantiomers and diastereomers. The stereoisomers of the instant invention are named according to the Cahn-Ingold-Prelog System. While shown without respect to stereochemistry in formulas (I), (II) and (VIII), the present invention includes all the individual possible stereoisomers; as well as the racemic mixtures and other mixtures of R and S stereoisomers (scalemic mixtures which are mixtures of unequal amounts of enantiomers) salts thereof. It should be noted that stereoisomers of the invention having the same relative configuration at a chiral center may nevertheless have different R and S designations depending on the substitution at the indicated chiral center.

The foregoing method also includes the preparation and forming of salts of the compounds of formulas (I), (II) and (VI). As a base, quinoline can form various acid salts. The salts of the compounds of formulas (I), (II) and (VIII) may be readily prepared by methods known to those persons of ordinary skill in the art. For the purpose of this invention, salts are those derived from organic and inorganic acids. Such organic and inorganic acids may be acetic, lactic, citric, tartaric, succinic, maleic, malonic, gluconic, hydrochloric, hydrobromic, phosphoric, nitric, sulfuric, methanesulfonic, and similarly known acceptable acids. Common mineral acids are HCl, HSO and $HNO_3$. These lists are intended only to provide examples and are not intended to be exhaustive. Thus, the present invention should not be viewed as limited to these examples.

General Synthesis

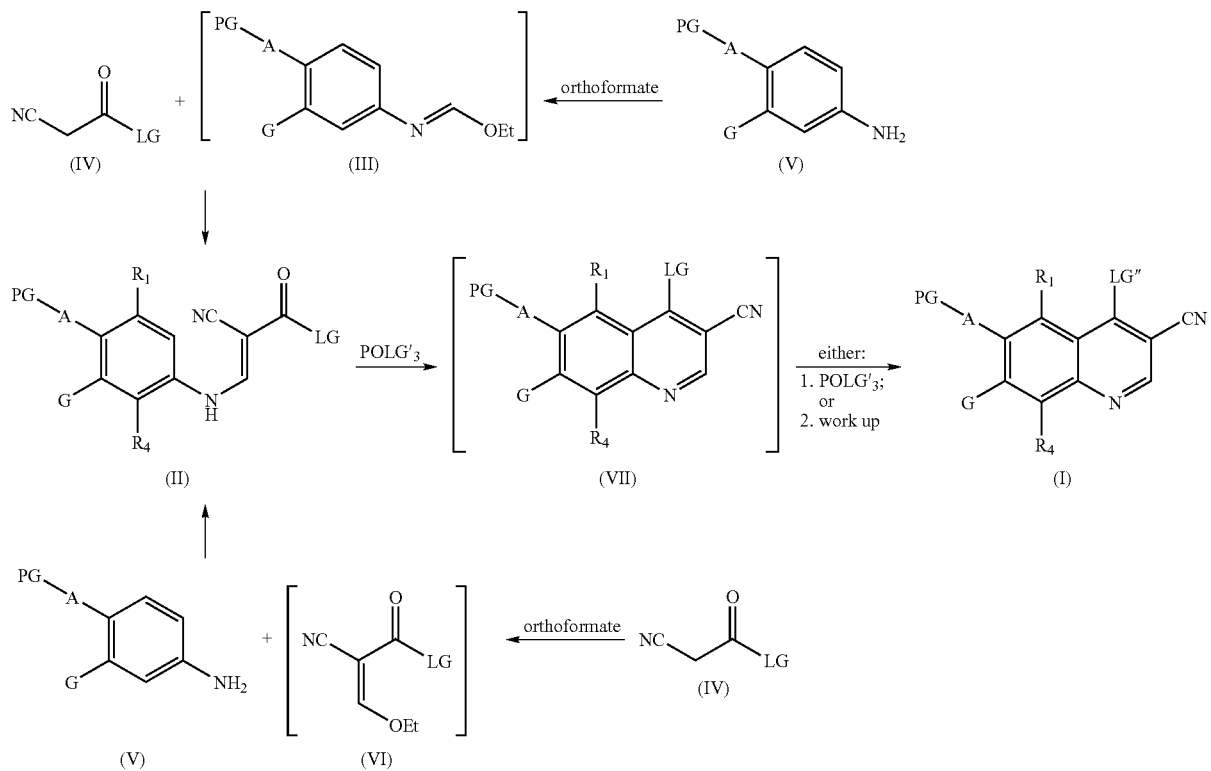

Scheme 1

Scheme 1 illustrates, in part, the synthesis of a 4-substituted quinoline compound of formula (I) from the starting protected aryl-2-propenamide compound of formula (II).

As shown in Scheme 1, an aryl-2-propenamide compound of formula (II) is treated with a phosphoryl halide through a Bischler-Napieralski reaction, which results in a compound of formula (I) that is halogenated at the 4-position. See Bischler, A., Napieralski, B, Ber., 26, 1903 (1893), which is incorporated herein by reference, for a general description of the Bischler-Napieralski reaction. However, the intermediate compound of formula (VII) can also be isolated, allowing for the synthesis of a quinoline with either a morpholine, a mesylate, a tosylate, or a triflate moiety at the 4-position.

These protected anilinoquinoline can be further reacted to form a 4-substituted quinoline in the presence of a catalytic amount of acid, such as methylsulfonic acid, pyridinium hydrochloride, hydrochloric acid, sulfuric acid or trifluoroacetic acid, and a nucleophilic reagent of formula HZ—(CH$_2$)$_n$X, wherein Z can be NR, O or S, n is 0 or 1, and X can be cycloalkyl of 3 to 7 carbon atoms, which may be optionally substituted with one or more alkyl of 1 to 6 carbon atom groups, or is a pyridinyl, pyrimidinyl, or phenyl ring, wherein the pyridinyl, pyrimidinyl, or phenyl ring may be optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or X can be a bicyclic aryl or bicyclic heteroaryl ring system of 8 to 12 atoms, where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkyl amino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or X can be a radical having the formula:

$$A'{-}T{-}L,$$

wherein A' is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamnino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, T is bonded to a carbon of A' and is:

—NH(CH$_2$)$_m$—, —(CH$_2$)$_m$—, —S(CH$_2$)$_m$—, —NR(CH$_2$)$_m$—,
—(CH$_2$)$_m$— —(CH$_2$)$_m$NH—, —(CH$_2$)$_m$O—, —(CH$_2$)$_m$S—, or —(CH$_2$)$_m$NR—;

and L is an unsubistituted phenyl ring or a phenyl ring mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or L can be a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkylof 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino.

In another preferred embodiment, the phosphoryl halide used in the above Bischler-Napieralski reaction is phosphoryl chloride.

For purposes of this invention, a leaving group is a labile atom or a group of atoms that can be charged or uncharged, that departs during a substitution or displacement reaction. For the foregoing method, suitable leaving groups may be halo, morpholino, o-mesyl, o-tosyl, or a triflate.

In a preferred embodiment, the leaving group is morpholino.

As shown in Scheme 1, the aryl-2-propenamide compound of formula (II) may be prepared by various reaction pathways, as described in the following Schemes 2 and 3.

Scheme 2

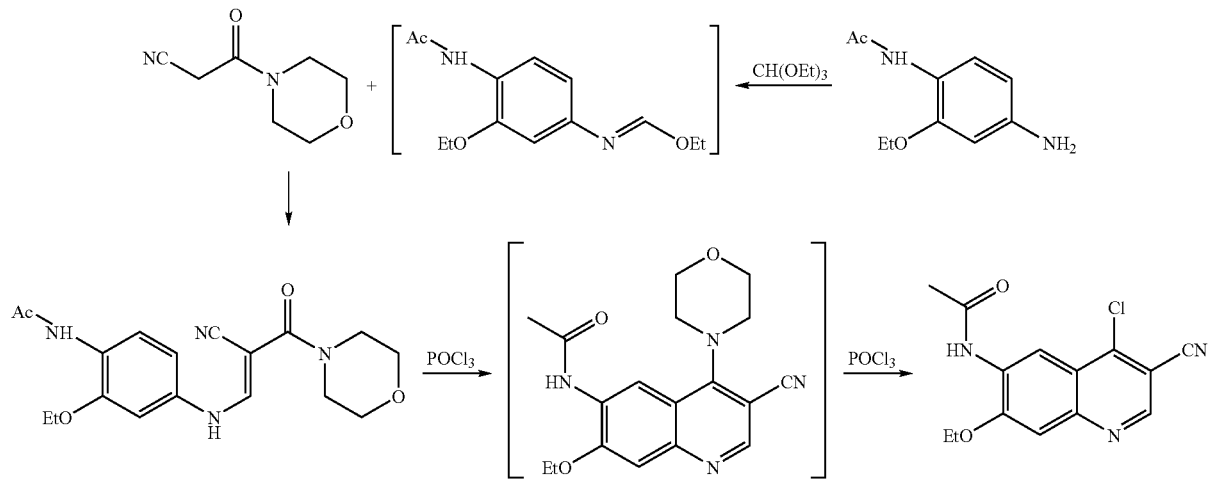

Scheme 2 illustrates one pathway to form an aryl-2-propenamide compound of formula (II) followed by the synthesis of a 4-halogenated quinoline compound of formula (I).

As shown in Scheme 2, arylamines are reacted with orthoformate to prepare arylformimidates. The arylformimidates are then condensed with active methylene compounds (e.g., cyanoacetylmorpholine to provide aryl-2-propenamides of formula (II). Through a Bischler-Napieralski reaction, treatment of the aryl-2-propenamides with a phosphoryl halide (e.g., phosphoryl chloride) results in 4-halogenated quinolines (e.g., 4-chloroquinolines).

Scheme 3

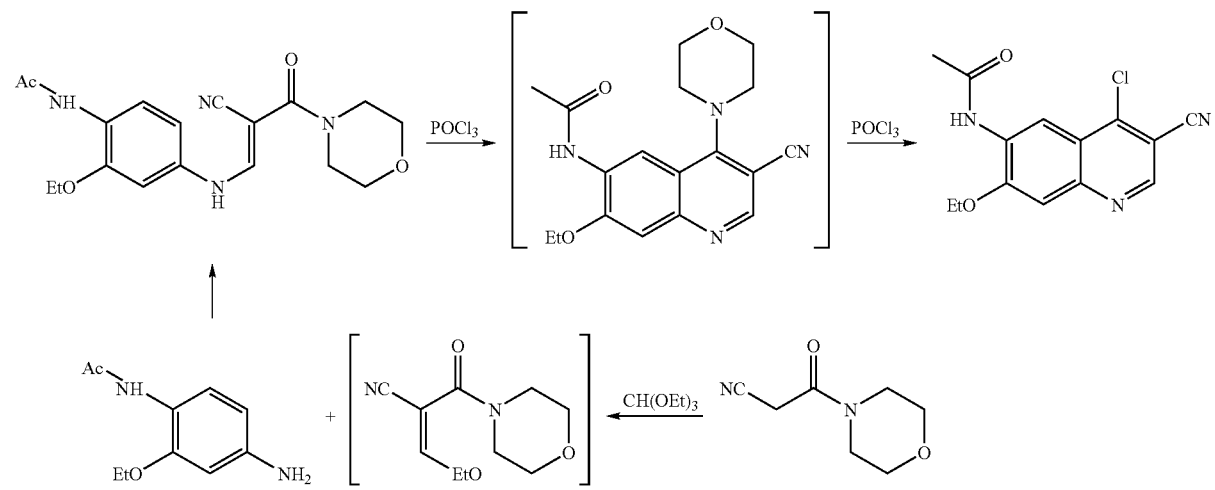

Scheme 3 illustrates a second pathway to form an aryl-2-propenamide compound of formula (II) followed by the synthesis of a 4-halogenated quinoline compound of formula (I).

As shown in Scheme 3, active methylene compounds (e.g., cyanoacetyl morpholine) are condensed with orthoformate to produce alkoxymethylene derivative compounds. These alkoxymethylene derivative compounds are further reacted with arylamines to give aryl-2-propenamides of formula (II). Through a Bischler-Napieralski reaction, treatment of the aryl-2-propenamides with a phosphoryl halide (e.g., phosphoryl chloride) results in 4-halogenated quinolines (e.g., 4-chloroquinolines).

The following examples are set forth to aid in an understanding of the invention, and are not intended, and should not be construed, to limit in any way the invention set forth in the claims that follow thereafter.

EXAMPLE 1

Synthesis of 6-acetamido-4-chloro-3-cyano-7-ethoxyquinoline

Preparation of 4-cyanoacetylmorpholine

A 4-neck 500 mL flask was charged with morpholine (77.0 g, 0.088 mol). Ethylcyanoacetate (100.0 g, 0.088 mol) was added. After addition, the reaction mixture was stirred. The mixture progressively turned yellow to clear. The mixture was heated to 100 to 110° C. for 3.0 hours. A solid formed after cooling to room temperature. Ethyl acetate (150 ml) and heptanes (300 ml) were added and the mixture stirred for 30 minutes at room temperature. The solid was filtered to give 95.2 g (71% yield) of 4-cyanoacetylmorpholine. $^1$H NMR: δ (DMSO-$d_6$) 4.02 (s, 2H); 3.37 (m, 2H); 3.55 (m, 4H); 3.45 (m, 2H).

Preparation of Propenamide

A 4-neck 250 mL flask was charged with 4-cyanoacetylmorpholine (7.21 g, 0.047 mol), aniline (10.0 g, 0.051 mol) and EPA (72 mL). The flask was equipped with an agitator, thermocoupler and $N_2$ protection. The mixture was heated to 50-60° C. The first of three portions of triethyl orthoformate (7.8 ml) was added. After one hour, the second portion of triethyl orthoformate (7.8 ml) was added. After another hour, the third portion of triethyl orthoformate (7.8 ml) was added. The resulting solution was held to 80° C. for 21 hours. Brown solids formed after cooling to room temperature. The solids were filtered, washed with IPA (2×15 mL) and dried to give 8.43 g (51% yield) of the desired compound. $^1$H NMR: δ (DMSO-$d_6$) 10.69 (d, 1H); 8.93 (s, 1H,); 8.30 (d, 1H); 7.82 (d, 1H); 6.86 (dd, 1H); 4.13 (q, 2H); 3.61 (m, 8H); 2.07 (s, 3H); 1.37 (t, 3H).

Preparation of 6-acetamido-4-chloro-3-cyano-7-ethoxyquinoline

To a 3-necked 50 ml flask equipped with an agitator, temperature probe, condenser and nitrogen protection was charged propenamide (2.0 g, 5.58 mmole) and suspended in acetonitrile (16 ml). The mixture was heated to 60-65° C. and phosphorus oxychloride (2.57 g, 1.56 ml, 3.0 eq, d=1.645 g/ml) was added dropwise over 2 mins. The mixture becomes clear and deep red within 30 mins. The mixture was held for 14 hours and then cooled to 0-15° C. Water (5 ml) was added keeping the pot temperature <20° C. The pH was adjusted to 8-10 using either 8% aqueous potassium carbonate or 50% aqueous sodium hydroxide. The mixture can be treated under various workup conditions listed below:

1. The organic solvent was removed on a rotary evaporator. Toluene (20 ml) is added the mixture stirred for I hour at room temperature then filtered and washed with water (25 ml) and heptane (2×25 ml). The solids are dried overnight at 55-60° C. with full vacuum to give crude product.

2. Alternatively, isopropyl acetate (30 ml) was added and the mixture stirred for a minimum of 30 mins. The pH was re-checked to make sure it remained at 8-10. Additional aqueous potassium carbonate may be added if necessary. The layers were separated and the organic phase washed with water (2×30 ml) and brine (30 ml). To the organic phase was added silica gel 60 (30 g) and the mixture stirred for a minimum of 30 mins. The mixture was filtered and washed with isopropyl acetate (30 ml). The organic phase was concentrated to dryness to give crude compound. This workup still left small amounts of polar impurities in the product.

What is claimed is:

1. A method of preparing a 4-substituted quinoline compound of the following formula (VIII):

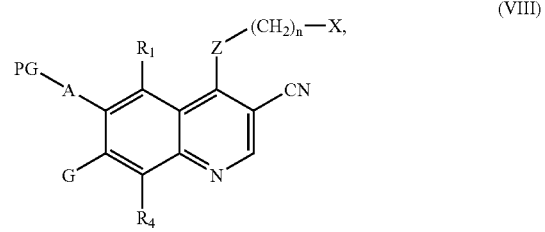

said method comprising the steps of:

a. reacting a compound of formula (I):

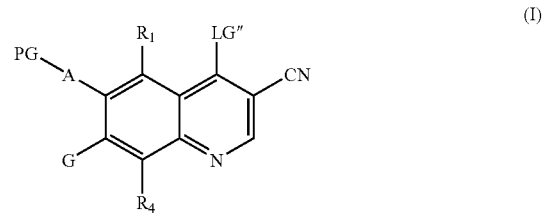

with a nucleophilic reagent of formula HZ-$(CH_2)_n$—X to produce the compuond of formula (VIII); or b(i). reacting a compound of formula (II):

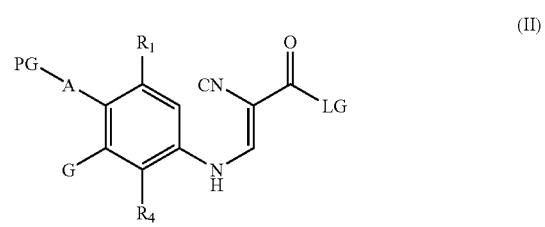

with a nucleophilic reagent of formula HZ-$(CH_2)_n$—X to form a compound of formula (IX):

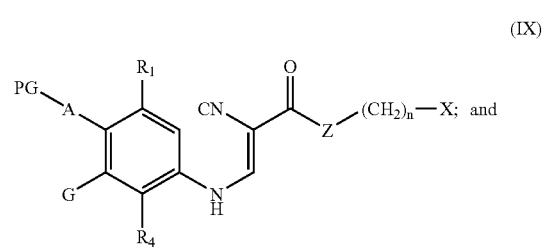

b(ii). cyclizing the compound of formula (IX) with a reagent of formula POLG' to produce the compound of formula (VIII)

wherein:
- LG is a leaving group selected from the group consisting of morpholino, o-mesyl, o-tosyl, triflate;
- LG' is halo;
- LG" is a leaving group selected from the group consisting of morpholino, o-mesyl, o-tosyl, triflate and halogen;
- PG is a protecting group selected from the group consisting of acyl, $CH_3OC(O)-$, $EtOC(O)-$, Fmoc, trifluoroacetamide, Troc, Phenoc, benzamide, Teoc and cyclic imides such as pthalimide, maleimide and 2,5-dimethylpyrrole;
- A is O, NR, or S;
- R is H, alkyl, alkenyl, or alkynyl; and
- G, $R_1$ and $R_4$ are each, independently, hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phthalimide, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

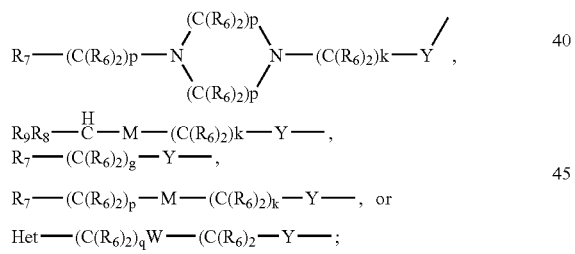

or $R_1$ and $R_4$ are as defined above and G is $R_2-NH-$;
or if any of the substituents $R_1$, $R_4$ or G are located on contiguous carbon atoms then they may be taken together as the divalent radical $-O-C(R_6)_2-O$;
Y is a divalent radical selected from the group consisting of $-(CH_2)_a-$, $-O-$, and $-\underset{R_6}{\underset{|}{N}}-$;

$R_7$ is $-NR_6R_6$, $-OR_6$, -J, $-N(R_6)_3^+$, or $-NR_6(OR_6)$;
M is $>NR_6$, $-O-$, $>N-(C(R_6)_2)_pNR_6R_6$, or $>N-(C(R_6)_2)_p-OR_6$;
W is $>NR_6$, $-O-$ or is a bond;
Het is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

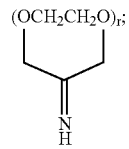

wherein Het is optionally mono- or di-substituted on carbon or nitrogen with $R_6$, optionally mono- or di-substituted on carbon with hydroxy, $-N(R_6)_2$, or $-OR_6$, optionally mono or di-substituted on carbon with the mono-valent radicals $-(C(R_6)_2)_sOR_6$ or $-(C(R_6)_2)_sN(R_6)_2$, and optionally mono or di-substituted on a saturated carbon with divalent radicals $-O-$ or $-(C(R_6)_2)_sO-$;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms; with the proviso that the alkenyl or alkynyl moiety is bound to a nitrogen or oxygen atom through a saturated carbon atom;

$R_2$, is selected from the group consisting of

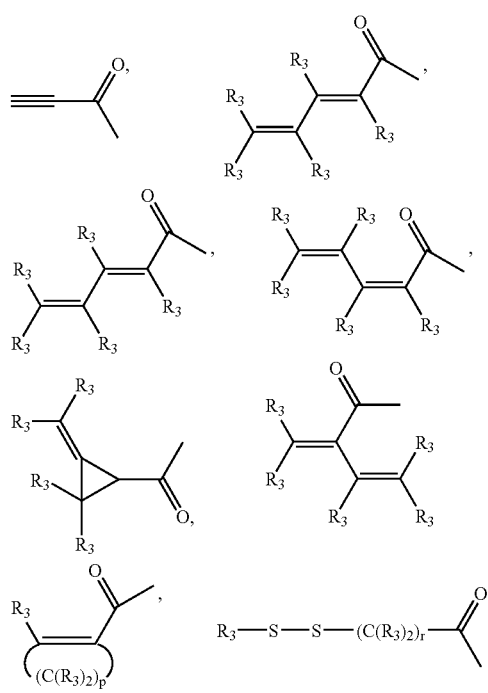

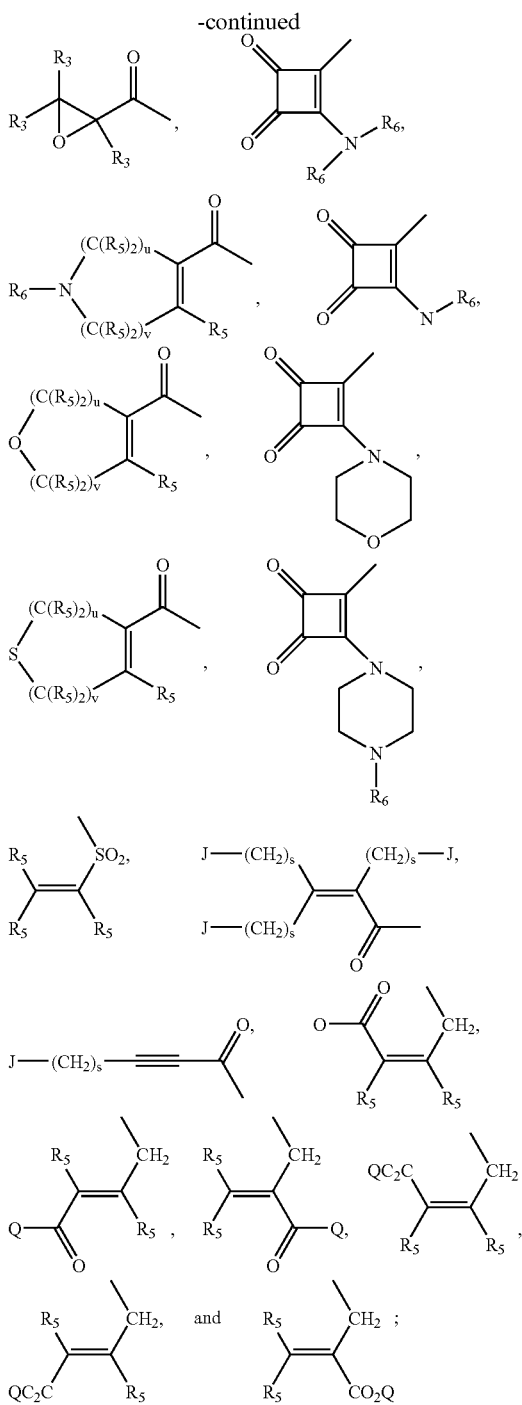

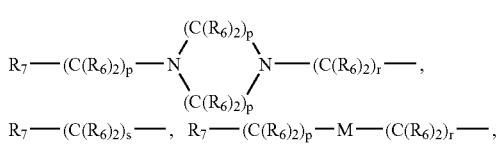

$R_3$ is independently hydrogen, alkyl of 1-6 carbon atoms, carboxy, carboalkoxy of 1-6 carbon atoms, phenyl, carboalkyl of 2-7 carbon atoms,

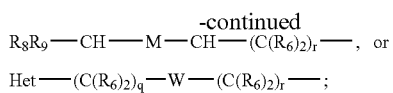

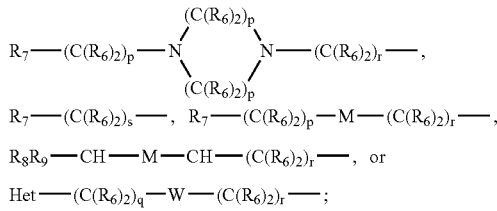

$R_5$ is independently hydrogen, alkyl of 1-6 carbon atoms, carboxy, carboalkoxy of 1-6 carbon atoms, phenyl carboalkyl of 2-7 carbon atoms, $R_8$, and $R_9$ are each independently $-(C(R_6)_2)_r NR_6R_6$, or $-(C(R_6)_2)_r OR_6$;

J is independently hydrogen, chlorine, fluorine, or bromine;

Q is an alkyl of 1-6 carbon atoms or hydrogen;

a=0 or 1;

g=1-6;

k=0-4;

n is 0-1;

m is 0-3;

p=2-4;

q=0-4;

r=1-4;

s=1-6;

u=0-4 and v=0-4, wherein the sum of u+v is 2-4;

x=0-3;

y=0-1;

z=0-3;

Z can be NR, O or S;

n is 0 or 1; and

X can be cycloalkyl of 3 to 7 carbon atoms, which may be optionally substituted with one or more alkyl of 1 to 6 carbon atom groups, or is a pyridinyl, pyrimidinyl, or phenyl ring, wherein the pyridinyl, pyrimidinyl, or phenyl ring may be optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or X can be a bicyclic aryl or bicyclic heteroaryl ring system of 8 to 12 atoms, where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkyl amino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or X can be a radical having the formula:

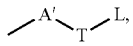

wherein A' is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamnino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, T is bonded to a carbon of A' and is:

—NH(CH$_2$)$_m$—, —O(CH$_2$)$_m$—, —S(CH$_2$)$_m$—, —NR(CH$_2$)$_m$—,
—(CH$_2$)$_m$— —(CH$_2$)$_m$NH—, —(CH$_2$)$_m$O—, —(CH$_2$)$_m$S—, or
—(CH$_2$)$_m$NR—, and L is an unsubsititued phenyl ring or a phenyl ring mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino, or L can be a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkylof 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino;

or a salt thereof.

2. The method of claim 1, wherein LG' is chloro.

* * * * *

UNITED STATES PATENT AND TRADEMARK OFFICE
CERTIFICATE OF CORRECTION

| | | |
|---|---|---|
| PATENT NO. | : 7,432,377 B2 | Page 1 of 2 |
| APPLICATION NO. | : 11/036408 | |
| DATED | : October 7, 2008 | |
| INVENTOR(S) | : Warren Chew et al. | |

It is certified that error appears in the above-identified patent and that said Letters Patent is hereby corrected as shown below:

<u>COLUMN 1</u>:

Line 28, "over expression," should read --overexpression,--; and
Line 34, "over expression" should read --overexpression--.

<u>COLUMN 3</u>:

Line 45, "—$NR_6$," should read -- —$NR_6R_6$,--; and
Line 49, "NR6," should read --$NR_6$--.

<u>COLUMN 12</u>:

Line 7, "consist" should read --consists--;
Line 8, "consist" should read --consists-- and "a" should read --an--;
Line 29, "consist" should read --consists--;
Line 30, "consist" should read --consists-- and "a" should read --an--;
Line 50, "consist" should read --consists--;
Line 61, "a" should read --an--; and
Line 62, "a" should read --an--.

<u>COLUMN 15</u>:

Line 14, "These" should read --This--.

<u>COLUMN 21</u>:

Line 10, "pthalimide," should read --phthalimide,--.

UNITED STATES PATENT AND TRADEMARK OFFICE
CERTIFICATE OF CORRECTION

PATENT NO.         : 7,432,377 B2
APPLICATION NO. : 11/036408
DATED                 : October 7, 2008
INVENTOR(S)       : Warren Chew et al.

It is certified that error appears in the above-identified patent and that said Letters Patent is hereby corrected as shown below:

COLUMN 22:

Line 20, "—(C" should read -- —O(C--.

Signed and Sealed this

Twenty-fourth Day of March, 2009

JOHN DOLL
*Acting Director of the United States Patent and Trademark Office*